(12) United States Patent
Huang et al.

(10) Patent No.: US 11,389,500 B2
(45) Date of Patent: Jul. 19, 2022

(54) LIQUID INVISIBLE MASK WITH BROAD-SPECTRUM BACTERIOSTASIS AND PREPARATION METHOD AND USING METHOD THEREOF

(71) Applicant: Hunan Tianxiang Biotechnology Co., Ltd, Shaoyang (CN)

(72) Inventors: Mingyong Huang, Shaoyang (CN); Minda Huang, Shaoyang (CN); Yabo Guo, Shaoyang (CN); Furong Yue, Shaoyang (CN); Shulan Yuan, Shaoyang (CN)

(73) Assignee: Hunan Tianxiang Biotechnology Co., Ltd, Shaoyang (CN)

( * ) Notice: Subject to any disclaimer, the term of this patent is extended or adjusted under 35 U.S.C. 154(b) by 0 days.

(21) Appl. No.: 17/488,449

(22) Filed: Sep. 29, 2021

(65) Prior Publication Data

US 2022/0040249 A1 Feb. 10, 2022

(30) Foreign Application Priority Data

Aug. 5, 2020 (CN) .......................... 202010777733.1

(51) Int. Cl.
*A61K 36/88* (2006.01)
*A61K 31/10* (2006.01)
*A61K 36/185* (2006.01)

(52) U.S. Cl.
CPC .............. *A61K 36/88* (2013.01); *A61K 31/10* (2013.01); *A61K 36/185* (2013.01); *A61K 2236/37* (2013.01); *A61K 2236/51* (2013.01)

(58) Field of Classification Search
None
See application file for complete search history.

(56) References Cited

FOREIGN PATENT DOCUMENTS

| CN | 202590009 U | 12/2012 |
| CN | 206371555 U | 8/2017 |
| CN | 208799691 U | 4/2019 |

*Primary Examiner* — Russell G Fiebig

(57) ABSTRACT

A liquid invisible mask, and a preparation method and a using method thereof are provided by the present disclosure, and the present disclosure relates to the technical field of isolated bacteriostatic protective materials. The liquid invisible mask which is a film covering a surface of a nasal cavity, an oral cavity or a throat mucosa, wherein: the film comprises a garlic extract with garlicin content more than 45%, sesame essential oil and cream; and a mass ratio of the garlic extract, the sesame essential oil and the cream is (70-85): (10-20): (5-10). The present disclosure takes the garlic extract with high content of garlicin as the active component, ensures the basic efficacy of sterilization and toxicity elimination, and is supplemented with sesame essential oil as the film-forming carrier material and cream as the skeleton material.

7 Claims, 3 Drawing Sheets

LIQUID INVISIBLE MASK WITH BROAD-SPECTRUM BACTERIOSTASIS AND PREPARATION METHOD AND USING METHOD THEREOF

CROSS-REFERENCE TO RELATED APPLICATIONS

The application claims priority to Chinese patent application No. 202010777733.1, filed on Aug. 5, 2020, the entire contents of which are incorporated herein by reference.

TECHNICAL FIELD

The present disclosure relates to the technical field of isolated bacteriostatic protective materials, and particularly relates to a liquid invisible mask with broad-spectrum bacteriostasis, a preparation method and a using method thereof.

BACKGROUND

Nasal cavity is the two doors of respiratory tract. When the particles with small particle size enter the nasal cavity through the protective mask, some particles will be absorbed by the internal mucosa of the nasal cavity and blocked outside the upper respiratory tract. However, due to the limited adsorption capacity, there are still loopholes.

The existing commercially available masks are mainly divided into cotton masks, medical non-woven masks, activated carbon masks, anti-dust masks and N95 masks. Cotton masks are suitable for winter wear, mainly anti-freezing. Medical non-woven masks are mainly used to prevent bacteria, and 90% of 5 µm particles are removed, and still 10% of 5 µm particles will enter the nasal cavity. Activated carbon mask can absorb gas and odor, prevent dust, and can not filter particles and bacteria in the air. Anti-dust mask is usually used in the case of large dust, and equipped with a breathing valve, can make very good dust-proof effect. N95 mask can filter non-oil suspended particles in the air, the filtering effect reaches 95%, that is, still 5% of particles will come into the human respiratory system as a leakage. Research shows that the existing commercially available mask protection system has 5% to 10% of the protection loopholes, which will still lead to 5% to 10% of harmful particles (harmful dust, bacteria, virus, etc.) through the nasal cavity into the human respiratory system, causing infection and injury to the human body.

At present, nasal spray is mainly divided into two parts, one part is mainly for the purpose of treatment, using chemical drugs or active ingredients of traditional Chinese medicine to rapidly penetrate into the mucosa to improve nasal problems; although it is effective, there are certain side effects, so it can only be used for a short time and can not be used for a long time. The other part is mainly for protection, but the protection effect is poor, and the long-term use safety is difficult to guarantee; for example, a nasal spray with high efficiency for filtering air pollutants is made of onion/garlic extract, natural sea salt, hyaluronic acid and ultrapure water; and the test results showed that the highest bacteriostasis and sterilization rate was only 69% (Embodiment 4), and natural sea salt and hyaluronic acid were added, which were not suitable for long-term use as protective articles; in addition, because of the existence of garlicin, the irritation was too strong, which easily caused the user to sneeze, resulting in the loss of the drug film originally covering the nasal cavity, and could not play a long-term protective effect.

In the prior art, it is proposed to add more auxiliary material to nasal spray containing allitridin to alleviate irritation, for example, a medical biological antibacterial dressing and adopts modified chitosan and garlic extract compound for synergistic sterilization. In addition, camellia oil, olive oil and almond oil are supplement for moisturizing, moistening and film-forming, and peppermint oil, star anise oil, momordica grosvenorii extract, liquorice extract and alum are added to assist sterilization and bacteriostasis, alleviate irritation and mask garlic taste. But in the actual research, it was found that the stability of the film layer was poor, and the bactericidal effect of modified chitosan and garlic extract was lost without fully playing, resulting in the user had to supplement the liquid medicine several times a day, greatly increasing the economic cost; and more importantly, because of the addition of modified chitosan and a large number of excipients, the long-term safety can not be guaranteed.

SUMMARY

The first object of the present disclosure is to provide a liquid invisible mask with a broad-spectrum bacteriostasis function with high safety, long protection time-effect and good comfort under long-term use.

The liquid invisible mask which is a film covering a surface of a nasal cavity, an oral cavity or a throat mucosa, wherein: the film comprises a garlic extract with garlicin content more than 45%, sesame essential oil and cream; and a mass ratio of the garlic extract, the sesame essential oil and the cream is (70-85): (10-20): (5-10).

The present disclosure adopts the bionics principle and the TRIZ innovation theory, combines the nasal cavity structure and the function with the protective effect of the mask, uses a natural and safe small molecular plant extract as the raw material, and forms a stable liquid with long-term broad-spectrum antibacterial and bacteriostatic effect through scientific formula, thereby innovating the use method of the invisible mask.

In the present disclosure, the garlic extract with high content of garlicin is used as the active component to ensure high bactericidal and toxin-killing effect; meanwhile, the sesame essential oil is selected as the film-forming carrier material and the cream is selected as the skeleton material; through the synergistic effect of the three materials, the bactericidal and bacteriostatic effect is improved, and the safety of the film layer is remarkably improved; and there is no side effect after long-term use. Furthermore, based on the specific selection of film carrier materials and framework materials, the adsorption performance of the film layer to dust and droplets, the embedding bacteriostatic ability of the film layer to pathogenic microorganisms, the self-stability of the film layer and the adhesion of the film layer to the mucosa can be significantly improved, so that the overall protective performance of the liquid mask can be significantly improved. In addition, the sesame essential oil and the cream have the function of coordinating garlic flavor, eliminating the irritation of garlic to the user, increasing the comfort of use, so as to maximize the long-term protection function and achieve remarkable effect.

Specifically, the sesame essential oil can promote the uniform dispersion of the garlicin oil in the film layer, improve the bactericidal and bacteriostatic effect of the garlicin, and can effectively adsorb the particulate matter dust and the droplet in the air entering the nasal cavity, and can also embed the pathogenic microorganism to inactivate, so as to effectively block and clear the pathogenic microorganism, protect the nasal mucosa, and achieve the purpose of avoiding the nasal cavity and respiratory tract infection.

The cream plays a supporting role on the film layer, improves the stability of the film layer, and cooperates with the sesame essential oil to improve the adsorption of the film layer on dust and droplets; more importantly, the skeleton material can not only make the film layer more stably adhere to the surface of the mucosa, but also can prevent garlicin from being absorbed by the mucosa, reduce the loss of garlicin content while reducing the sense of stimulation, so as to play a long-term bactericidal and bacteriostatic mechanism, and make up for the protection defects of the mask filtering air. The liquid invisible mask of the present disclosure has the advantages of safety and environmental protection, long time effect, easy removal, and no limitation on the use of the traditional mask and the defect that the waste causes secondary pollution to the environment.

The garlic extract is a natural small molecule activeolecule active material, and the garlic extract obtained from purple garlic is preferable, so that the bacteriostatic effect is more obvious; meanwhile, the garlic extract contains more abundant anthocyanin, has a certain antioxidant effect, and can prevent the oil from being oxidized during long-term storage.

The garlic extract is preferably extracted by a high-pressure water-oil mixed phase extraction technique. Specifically, the detailed steps are as follows: mixing garlic and extract solution in a weight ratio of 1:(2-5), extracting in a high-pressure water-oil mixed phase, and extracting for 5 h to 12 h under an action of an extraction pressure difference formed by an operation of a high-pressure rotor pump; separating an extracted material and solution, standing the extract solution, layering water-oil, and an oil layer is garlic oil; wherein, drying and crushing the garlic to 60 meshes to 80 meshes; preparing the extract solution in a weight ratio of water:edible refined rapeseed oil as 1:(1-5); a vacuum degree generated by the operation of the high-pressure rotor pump is 0.02 MPa to 0.08 MPa, and a discharge pressure is 0.1 MPa to 0.6 MPa.

Content of the garlic extract is 70% to 85% of a total mass of the liquid invisible mask, and preferably is 80% to 85% of the total mass of the liquid invisible mask.

The sesame essential oil can be obtained by physical press method, and the characteristic indexes are: specific gravity (20/4° C.): 0.9126~0.9287; refractive index (20° C.): 1.4792~1.4791.

Content of the sesame essential oil is 10% to 20% of the total mass of the liquid invisible mask, and preferably is 10% to 15% of the total mass of the liquid invisible mask.

As an embodiment of the present disclosure, a mass ratio of the garlic extract to the sesame essential oil is (80-85):(10-15). The results showed that garlicin could be dispersed evenly in the film layer, and garlicin could be fully used to bactericidal and bacteriostatic effect on the bacteria and viruses embedded in the film layer. The overall bactericidal and bacteriostatic effect was better.

The cream is preferably extract from natural fresh milk, and has a soft yellow luster on the surface, has a milk fragrance, and contains vitamin A and E naturally present in milk, and the cream is free of any pigment and chemical stabilizer, and is beneficial to human health. As a skeleton material, the cream can not only improve the stability of the film layer and the adhesion to the mucosa, but also use the milk fragrance to effectively cover the garlic smell, and can also improve the comfort of use.

Before using, the cream must be dewatered so that the milk fat content is above 99.9%. Specifically: making the sterilized cream into cream grains, then melting, dehydrating and deproteinizing, and then concentrating in vacuum.

Content of the cream is 5% to 10% of the total mass of the liquid invisible mask, and preferably is 5% to 7%.

As the embodiment of the present disclosure, when the content of the garlic extract is high, the mass ratio of the sesame essential oil to the cream is (10-15):(5-10), at this time, the synergistic effect of the film-forming carrier material and the supporting material is better, not only the stability of the film layer is further improved, the loss of garlic is prevented, but also the adsorption of dust and droplets is stronger, the adhesion to the mucosa is better, and the overall protection effect is higher. Preferably, the mass ratio is (10-15):(5-7).

As the embodiment of the present disclosure, the mass ratio of the garlic extract, the sesame essential oil and the cream is (80-85):(10-15):(5-10). Preferably, the mass ratio is (80-85):(10-15):(5-7).

A second object of the present disclosure is aimed to provide a preparation method for the liquid invisible mask, comprising: refining the sesame essential oil at 120° C. to 125° C. for 20 min to 25 min and adding the cream, then continuing to refine for 10 min to 15 min, after cooling, adding the garlic extract, and then emulsifying and homogenizing to form a stable liquid state According to the characteristics of the raw materials, through repeated tests, it is determined that the emulsion homogenization adopts a batch homogenization treatment mode with a rotational speed of 1450-1500 r/min, so as to improve the stability of the mixed material (film layer structure).

Preferably, the intermittent homogenization process comprises three consecutive operating units, the specific start-up and standstill times being adjustable according to actual needs, such as start-up for 3 min and stop for 2 min.

The intermittent homogenizing treatment can use a common homogenizing emulsifier in the art, such as a pipeline high-shear homogenizing emulsifier, with a processing capacity of 500 L to 1000 L per hour.

A third object of the present disclosure is to provide a using method for the liquid invisible mask, comprising: spraying or smearing the liquid invisible mask to form the film in the nasal cavity, the oral cavity or a throat, at the same time, removing the film by soaking in warm water.

The benefits of the disclosure are as follows:

the liquid invisible mask according to the present disclosure not only has excellent bactericidal, bacteriostatic and adsorption effects, but also has high safety, long protection effect, small irritation and strong comfort for long-term use. The details are as follows:

(1) safety: the garlic extract, sesame essential oil and cream raw materials used for the liquid mask are edible raw materials, so they can be used for a long time and absorbed by the human body without any side effect.

(2) Effectiveness: the liquid invisible mask can be used in the nasal cavity, oral cavity, throat and other parts, and form a liquid protective film layer rich in small molecule active garlic extract in the mucosa and other parts, not only blocking the pathogenic microorganism virus and bacteria from infecting the human mucosal cells, but also utilizing the broad-spectrum bacteriostatic effect of the garlic extract to exert the effects of inhibiting and inactivating the pathogenic microorganism, thereby replacing the traditional mask, achieving the effective purpose of preventing and eliminating the pathogenic microorganism, and reducing the risk of infecting the human body and causing the disease.

(3) Invisible type: the liquid invisible mask can form a liquid protective film layer rich in small molecular substances in the nasal cavity, oral cavity, throat and other human mucosa parts, and its function is equivalent to the liquid mask of invisible film layer.

(4) Long acting time, comfortable and convenient to use: the liquid invisibility mask of the disclosure can adopt small package similar to a spray bottle, align with the protection part, spray 1 time to 2 times at most every day, which is comfortable to use and very convenient to carry.

(5) Environmental protection: since the film material and active ingredients can be absorbed and used by the human body and can be removed through warm water, medical garbage and secondary pollution to the environment caused by the disposable use of the mask are not transmitted.

DETAILED DESCRIPTION OF THE EMBODIMENTS

Figure 1:
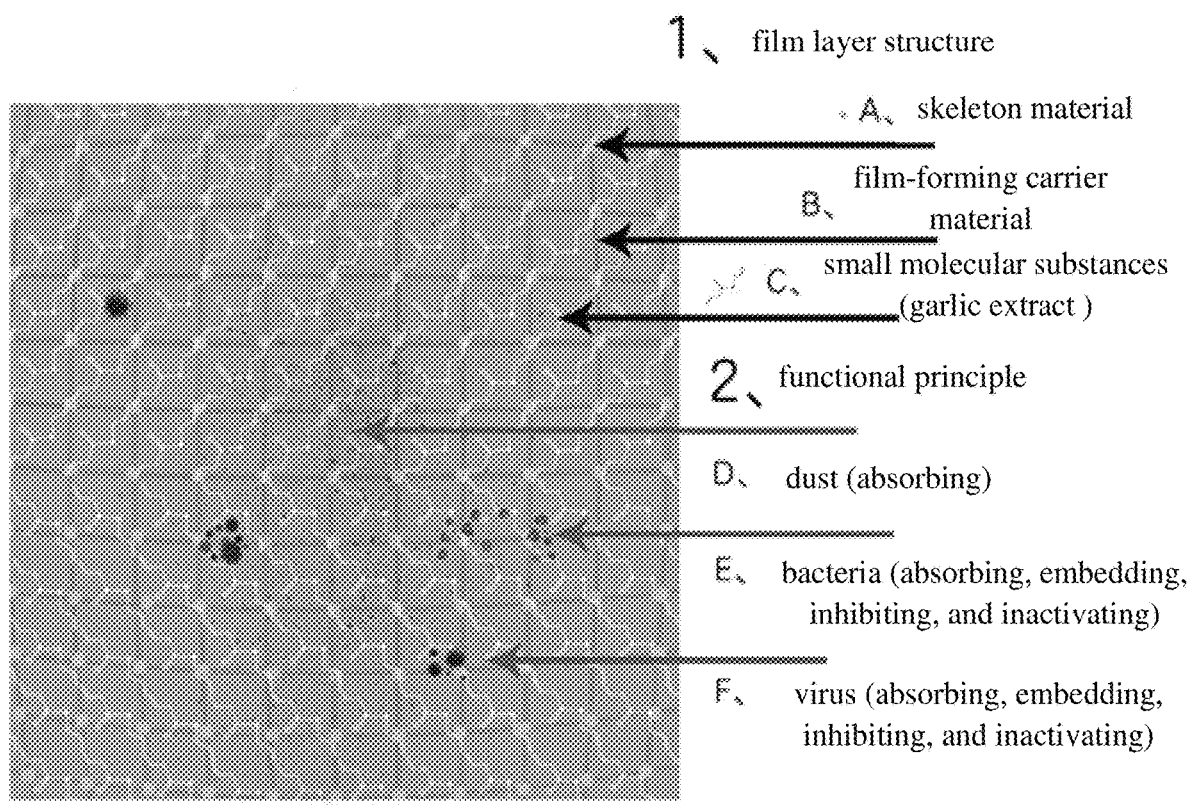
FIG. 1 is a schematic diagram of structure and functional principle of the liquid invisible mask in the embodiment 1 of the present disclosure.

The following embodiments are intended to illustrate the present disclosure, but are not intended to limit the scope of the present disclosure.

In the following embodiment, the garlic extract prepared by the following method:

selecting fresh purple garlic without pests and mildew in Longhui and Dongkou of selenium-rich soil area of Xuefeng Mountain, removing garlic peel, washing garlic with water and remove impurities such as sediment;

smashing the washed dry garlic, and using the electric hot air tunnel dryer for baking at the temperature of 60° C. for 12 h; and making mechanical crushing to 80 mesh;

putting the comminuted material into a stirring rotating leaf (36 r/min) leaching tank, adding the extract solution with the weight ratio of water to edible refined rapeseed oil as 1:5, and the weight ratio of garlic to the extract solution as 1:2; extracting for 8 h under an action of an extraction pressure difference formed by the high vacuum degree (0.02 MPa~0.08 MPa) and discharge pressure (0.1 MPa~0.6 MPa) produced continuously in an operation of the high-pressure rotor pump;

pressing the extracted material with a press to basically separate the product liquid; applying the residue to the subsequent processing of flavor sauce; leaving the separated extract liquid in a standing tank for 2 h to separate water and oil; testing the oil layer and preparing it into garlicin oil finished product with specific gravity 1.094 G/l~1.098 G/l, and refractive index (20° C.) 1.550118 4.5502.

Embodiment 1: a preparation method for the liquid invisible mask

The formula is as follows: according to the quality percentage, 85% garlic extract, 10% sesame essential oil and 5% cream.

Specific Preparation Steps:

1) refining the sesame essential oil in a thermostatic electric interlayer pot with stirring, a temperature 120° C., a time 20 min, then adding the cream, stirring for 10 min, and cooling for use;

2) adding the garlic extract in the 1), then emulsifying and homogenizing, and mixing evenly to form a stable liquid state.

Wherein, the pipeline high-shear homogenizing emulsifier is used for emulsifying and homogenizing, and the specific operating conditions are: speed 1450-1500R/min; intermittent operation: starting for 3 min, stopping for 2 min, continuing three operation units; and handling 500 L to 1000 L per hour.

Figure 2:
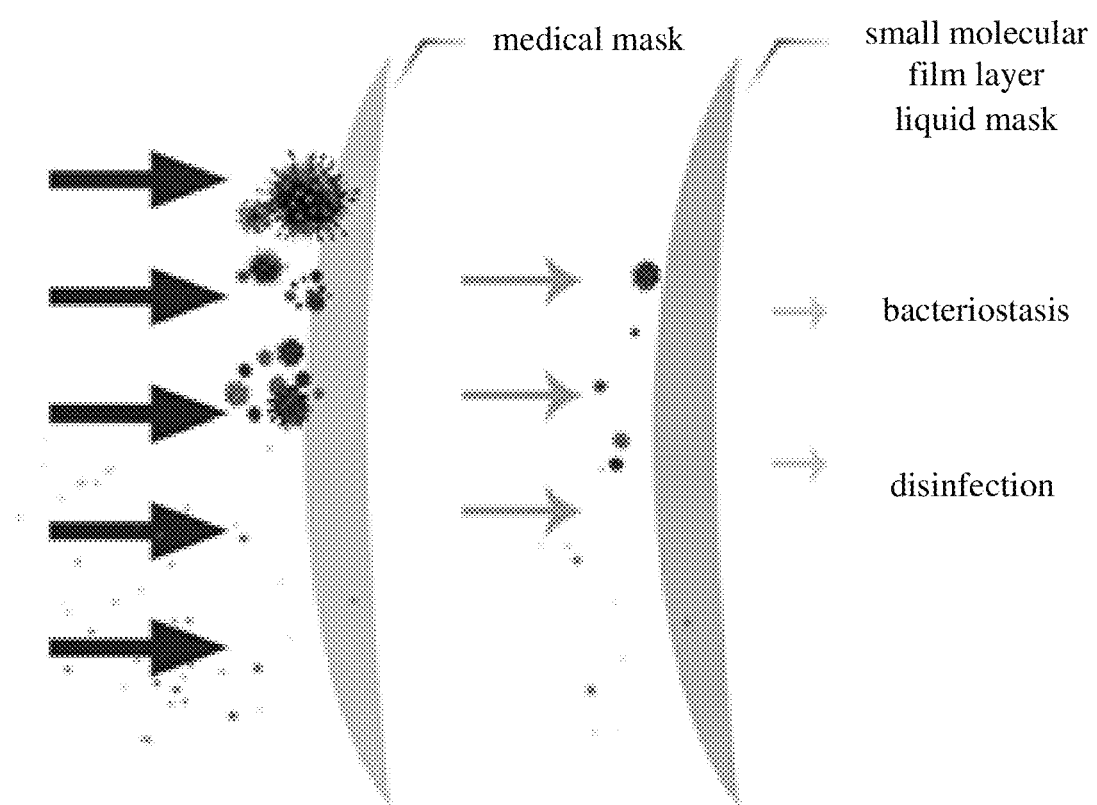
FIG. 2 is a use effect drawing of the liquid invisible mask in the embodiment 1 of the present disclosure in highly polluting environments.

FIG. 1 is a schematic diagram of structure and functional principle of the liquid invisible mask in the embodiment 1 of the present disclosure;

FIG. 2 is a use effect drawing of the liquid invisible mask in the embodiment 1 of the present disclosure in highly polluting environments; the highly polluting environment usually refers to a hospital or a crowded place. In a highly polluting environment, a layer of medical mask can be externally applied, and a layer of liquid invisible mask of the disclosure can be used inside, so as to play a double protection and be safer.

Figure 3:
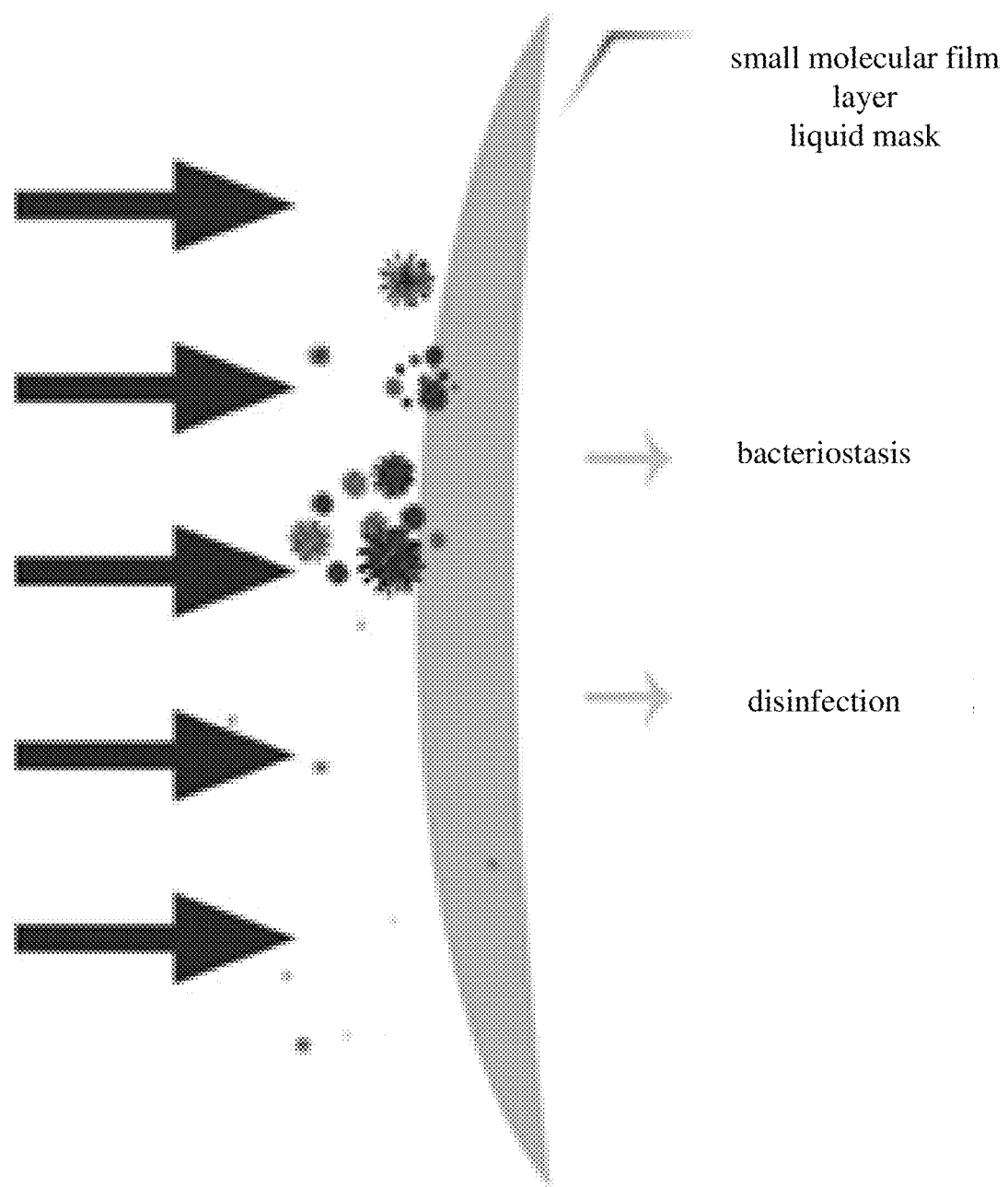
FIG. 3 is a use effect drawing of the liquid invisible mask in the embodiment 1 of the present disclosure in a normal environment.

FIG. 3 is a use effect drawing of the liquid invisible mask in the embodiment 1 of the present disclosure in a normal environment. In the normal environment, the liquid invisible mask can be used to replace the traditional external mask, and the protective film can be formed in the nasal cavity, the oral cavity, the throat and other parts of the user through the spraying equipment, so that most of the germs and dust can be isolated, and the susceptible population can be protected.

Embodiment 2: the preparation method for the liquid invisible mask

The preparation method is the same as Embodiment 1, and the difference is that the formula is as follows: according to the quality percentage, 70% garlic extract, 20% sesame essential oil and 10% cream.

Embodiment 3: the preparation method for the liquid invisible mask

The preparation method is the same as Embodiment 1, and the difference is that the formula is as follows: according to the quality percentage, 80% garlic extract, 15% sesame essential oil and 5% cream.

Effect Investigation

The protective effect, safety, irritation and other aspects of the liquid invisible mask obtained in Embodiment 1 and Embodiment 2 are tested.

1. Anti-Bacterial and Virus Inactivation

The test basis is GB15979-2002.

TABLE 1

Bacteriostatic Effect of Sample Stock Solution of Embodiment 1 on *Staphylococcus aureus*

| Test No. | Control group Number of colonies (CFU/mL) | Bacteriostatic rate for 5 min |
| --- | --- | --- |
| 1 | $1.87 \times 10^4$ | 86.31 |
| 2 | $2.81 \times 10^4$ | 85.69 |
| 3 | $3.29 \times 10^4$ | 85.07 |
| Average | $2.66 \times 10^4$ | 85.69 |

Note:
sterile growth of negative control

TABLE 2

Bacteriostatic Effect of Sample Stock Solution of Embodiment 1 on *Escherichia coli*

| Test No. | Control group Number of colonies (CFU/mL) | Bacteriostatic rate for 5 min |
|---|---|---|
| 1 | $4.25 \times 10^4$ | 91.20 |
| 2 | $2.40 \times 10^4$ | 93.12 |
| 3 | $3.17 \times 10^4$ | 91.82 |
| Average | $3.27 \times 10^4$ | 92.05 |

Note:
sterile growth of negative control

TABLE 3

Bacteriostatic Effect of Sample Stock Solution of Embodiment 1 on *Candida albicans*

| Test No. | Control group Number of colonies (CFU/mL) | Bacteriostatic rate for 5 min |
|---|---|---|
| 1 | $1.32 \times 10^4$ | 66.06 |
| 2 | $2.12 \times 10^4$ | 64.15 |
| 3 | $3.13 \times 10^4$ | 63.44 |
| Average | $2.25 \times 10^4$ | 64.55 |

Note:
sterile growth of negative control

TABLE 4

Virus Inactivation Rate Test of Sample Stock Solution of Embodiment 1 in 5 Min

| Laboratory virus and host | Action concentration and time | Group | virus titer logarithm lgTCID50/mL | Average virus titer logarithm lgTCID50/mL | Average total number of viruses TCID50/mL | Average inactivation logarithm (KL) | virus mortality rate (%) |
|---|---|---|---|---|---|---|---|
| Influenza A virus H1N1 (A/PR/8/34) Host name: MDCK cell | Stock Solution | Control group 1 | 6.12 | 5.94 | $9.15 \times 10^5$ | 1.04 | 90.05 |
| | | Control group 2 | 5.90 | | | | |
| | | Control group 3 | 5.80 | | | | |
| | | Group 1 | 4.80 | 4.9 | $9.10 \times 10^4$ | | |
| | | Group 2 | 5.20 | | | | |
| | | Group 3 | 4.71 | | | | |

TABLE 5

Test Effects of Samples Obtained in Embodiment 1 to Embodiment 2 and Comparative Embodiment

| | Antibacterial effect (5 min) % | | | 5 min virus extinguishing rate % H1N1 | Stability | Film-forming speed |
|---|---|---|---|---|---|---|
| | *Escherichia coli* | *Staphylococcus aureus* | *Candida albicans* | | | |
| Embodiment 1 | 92.05 | 85.69 | 64.55 | 90.05 | Hold for 9 h to 12 h | Very fast |
| Embodiment 2 | 85.05 | 76.03 | 54.55 | 80.16 | Hold for 6 h to 9 h | Relatively faster |
| Comparative Embodiment 1 | 68.35 | 62.25 | 48.36 | 60.05 | Hold for 5 min to 10 min Easily absorbed by skin and mucosa | General |
| Comparative Embodiment 2 | 72.34 | 65.38 | 46.72 | 73.38 | Hold for 10 min to 15 min | General |

Comparative Embodiment 1:

the preparation method is the same as Embodiment 1, and the difference is that the formula is as follows: according to the quality percentage, 55% garlic extract, 55% sesame essential oil and 15% cream.

Comparative Embodiment 2:

the preparation method is the same as Embodiment 1, and the difference is that the sesame essential oil is replaced with sweet orange oil, and the cream is replaced with cod liver oil.

The test effect of the sample obtained in Embodiment 3 is comparable to that of Embodiment 1 and Embodiment 2.

2. Mucosa Safety

According to the classification standard of eye irritation reaction in the Technical *Specification for Disinfection* (2002 edition), the product obtained in Embodiment 1 to Embodiment 3 is non-irritant in the damage type of New Zealand rabbit eyes.

3. Skin Irritation

According to the Evaluation Standard for Skin Irritation Intensity of the Technical *Specification for Disinfection* (2002 Edition), the product obtained in Embodiment 1 to Embodiment 3 is non-irritative to the multiple intact skin of New Zealand rabbits.

4. Stability and Long-Term Antibacterial Action

TABLE 6

Stability and long-term antibacterial action of Embodiment 1

| Antibacterial types | Antibacterial effect | | | | |
|---|---|---|---|---|---|
| | 5 min | 10 min | 15 min | 20 min | 8 h to 12 h |
| *Escherichia coli* | 92.05% | 99.36% | 99.94% | 99.99% | 99.99% |
| *Staphylococcus aureus* | 85.69% | 97.95% | 99.70% | 99.96% | 99.99% |
| *Candida albicans* | 64.55% | 87.43% | 95.54% | 99.01% | 99.99% |
| Influenza A virus H1N1 | 90.05% | 99.00% | 99.90% | 99.99% | 99.99% |

It can be seen from Table 6 that the long-acting bacteriostatic effect and stability of Embodiment 1 are remarkable, and the bacteriostatic and antiviral effects can reach 99.9% after 20 min of application; the liquid invisible mask formed in Embodiment 1 still has good antibacterial effect after 8 h to 12 h of application, which shows that the stability and long-acting bacteriostatic effect are very good. Meanwhile, the stability and long-term bacteriostatic effect of Embodiment 2 and Embodiment 3 are similar to those of Embodiment 1.

5. Garlicin Content

After testing, the content of the garlicin active ingredient in Embodiment 1 to Embodiment 3 is more than 45%, and the content of garlicin in the product of Embodiment 1 is 47.92%, which is 252 times of the content 0.19 of garlicin active ingredient in garlic.

6. Determination of Heavy Metals (Lead, Mercury and Arsenic)

Lead, mercury and arsenic are not detected in the product stock solution obtained in Embodiment 1 to Embodiment 3.

7. Microbiological Indicators

The total bacterial colony count and total fungal colony count of the product stock solution obtained in Embodiment 1 to Embodiment 3 are all less than 1 CFU/mL, and *Escherichia coli* group, *Staphylococcus aureus, Pseudomonas aeruginosa* and hemolytic *streptococcus* are not detected and meet the requirements of GB 15979-2002 *Hygienic Standard for Disposable Sanitary Articles*.

Although the present disclosure has been described in detail above with general description and specific embodiments, it will be apparent to those skilled in the art that some modifications or improvements may be made on the basis of the present disclosure. Therefore, these modifications or improvements made without departing from the spirit of the disclosure are within the scope of the disclosure.

We claim:

1. A liquid clear mask, which is a film covering a surface of a nasal cavity, an oral cavity or a throat mucosa, wherein: the film comprises a garlic extract with garlicin content more than 45%, sesame essential oil and cream; and a mass ratio of the garlic extract, the sesame essential oil and the cream is (70-85):(10-20):(5-10).

2. The liquid clear mask according to claim 1, wherein: content of the garlic extract is 70% to 85% of a total mass of the liquid invisible mask; content of the sesame essential oil is 10% to 20% of the total mass of the liquid invisible mask, and content of the cream is 5% to 10% of the total mass of the liquid invisible mask.

3. The liquid clear mask according to claim 2, wherein: a mass ratio of the garlic extract to the sesame essential oil is (80-85):(10-15).

4. The liquid clear mask according to claim 1, wherein: a mass ratio of the sesame essential oil to the cream is (10-15):(5-10).

5. The liquid clear mask according to claim 1, wherein: the mass ratio of the garlic extract, the sesame essential oil and the cream is (80-85):(10-15):(5-10).

6. The liquid clear mask according to claim 5, wherein: the mass ratio of the garlic extract, the sesame essential oil and the cream is (80-85):(10-15):(5-7).

7. The liquid clear mask according to claim 1, wherein: the garlic extract is obtained by following steps: mixing garlic and extract solution in a weight ratio of 1:(2-5), extracting in a high-pressure water-oil mixed phase, and extracting for 5 h to 12 h under an action of an extraction pressure difference formed by an operation of a high-pressure rotor pump; separating an extracted material and solution, standing the extract solution, layering water-oil, and an oil layer is garlic oil; wherein, drying and crushing the garlic to 60 meshes to 80 meshes; preparing the extract solution in a weight ratio of water:edible refined rapeseed oil as 1:(1-5); a vacuum degree generated by the operation of the high-pressure rotor pump is 0.02 MPa to 0.08 MPa, and a discharge pressure is 0.1 MPa to 0.6 MPa.

* * * * *